(12) United States Patent
Adams

(10) Patent No.: US 11,272,817 B2
(45) Date of Patent: Mar. 15, 2022

(54) COMBINATION TOILET WIPES PACKAGE WITH ATTACHED AIR FRESHENER FOR USE WITH A DISPENSER CONFIGURED TO ACCEPT THE PACKAGE

(71) Applicant: Jason R. Adams, Elk Grove, CA (US)

(72) Inventor: Jason R. Adams, Elk Grove, CA (US)

( * ) Notice: Subject to any disclaimer, the term of this patent is extended or adjusted under 35 U.S.C. 154(b) by 0 days.

(21) Appl. No.: 15/893,549

(22) Filed: Feb. 9, 2018

(65) Prior Publication Data

US 2019/0246849 A1 Aug. 15, 2019

(51) Int. Cl.
*A47K 10/42* (2006.01)
*A61L 9/12* (2006.01)
(Continued)

(52) U.S. Cl.
CPC .............. *A47K 10/421* (2013.01); *A61L 9/12* (2013.01); *B65D 75/5855* (2013.01);
(Continued)

(58) Field of Classification Search
CPC ............ A47K 10/421; A47K 2010/322; A47K 2010/3233; A47K 2010/3266; A61L 9/12;
(Continued)

(56) References Cited

U.S. PATENT DOCUMENTS 2,440,974 A 5/1948 Resch
2,539,059 A 1/1951 Cohn
(Continued)

FOREIGN PATENT DOCUMENTS

| CA | 2733869 | 1/2013 |
|---|---|---|
| DE | 2755332 A1 | 12/1977 |
| EP | 1989982 A2 | 12/2008 |

OTHER PUBLICATIONS

Website Link: https://www.pinterest.com/pin/273804852315308728/ Downloaded Mar. 28, 2016 Upcycled Can Toilet Paper Holder with Air Freshener Caddy.

(Continued)

*Primary Examiner* — Gene O Crawford
*Assistant Examiner* — Kelvin L Randall, Jr.
(74) *Attorney, Agent, or Firm* — Russ Weinzimmer & Associates, P.C.

(57) ABSTRACT

A combination toilet wipes package that also freshens the air of a bathroom. Some embodiments are suitable as a toilet wipes dispenser refill package. Some embodiments are suitable as a stand-alone toilet wipes dispenser package. The combination toilet wipes package includes a toilet wipes package having an opening on top for extracting moist toilet wipes contained therein, and an attached air freshener cartridge having a hole for allowing air freshener to diffuse out into the room. As a toilet wipes dispenser refill package, the combination toilet wipes package includes an air freshener cartridge having an air baffle ring configured to engage air baffle slots of a wipes dispenser. Some embodiments include a peel-away seal applied over both the opening of the toilet wipes package and the hole of the air freshener cartridge such that removing the seal opens both the package of moist toilet wipes and the air freshener cartridge.

6 Claims, 6 Drawing Sheets

(51) Int. Cl.
*B65D 75/58* (2006.01)
*B65D 83/08* (2006.01)
*A47K 10/32* (2006.01)

(52) U.S. Cl.
CPC .... *B65D 83/0805* (2013.01); *A47K 2010/322* (2013.01); *A47K 2010/3233* (2013.01); *A47K 2010/3266* (2013.01); *A61L 2209/133* (2013.01); *B65D 2575/586* (2013.01)

(58) Field of Classification Search
CPC ............ A61L 2209/133; B65D 5/4295; B65D 2203/12; B65D 2575/586; B65D 75/5855; B65D 83/0805
See application file for complete search history.

(56) References Cited

U.S. PATENT DOCUMENTS

| | | |
|---|---|---|
| 2,639,939 A | 5/1953 | Matchett |
| 2,901,790 A | 9/1959 | Nielsen |
| 3,192,008 A | 6/1965 | Dwyer |
| 3,368,522 A | 2/1968 | Cordis |
| 3,865,271 A | 2/1975 | Gold |
| 4,208,098 A * | 6/1980 | Johnson ................ G09F 19/00 359/467 |
| 4,375,317 A | 3/1983 | Funada et al. |
| 4,925,102 A | 5/1990 | Jones et al. |
| 5,311,986 A | 5/1994 | Putz |
| 5,439,521 A | 8/1995 | Rao |
| 5,624,025 A | 4/1997 | Hixon |
| 5,660,313 A | 8/1997 | Newbold |
| 5,894,001 A | 4/1999 | Hitzler et al. |
| 5,980,530 A | 11/1999 | Willard et al. |
| 6,056,235 A | 5/2000 | Brozinsky |
| 6,158,614 A * | 12/2000 | Haines ................ A47K 10/3818 221/33 |
| 6,189,730 B1 | 2/2001 | McClymonds |
| 6,536,707 B2 | 3/2003 | Adelakum |
| 6,568,625 B2 | 5/2003 | Faulks et al. |
| 6,655,630 B2 | 12/2003 | Newman et al. |
| 6,827,309 B1 | 12/2004 | Newman et al. |
| 6,883,787 B2 | 4/2005 | Allen |
| 6,959,890 B1 | 11/2005 | Breitinger |
| 7,717,258 B2 * | 5/2010 | Stephens ................ B65D 5/0227 206/213.1 |
| 7,832,555 B2 * | 11/2010 | Flannery ................ A47K 10/421 206/210 |
| 8,398,041 B2 | 3/2013 | Brinkdopke et al. |
| 8,496,881 B2 * | 7/2013 | Pohl ................ A01M 1/2061 422/125 |
| 8,602,244 B2 * | 12/2013 | Sanfilippo ................ B65B 1/02 220/6 |
| 8,893,920 B2 * | 11/2014 | Mothaffar ................ A47K 10/42 221/102 |
| 9,254,344 B2 * | 2/2016 | Hsu ................ A61L 9/03 |
| 9,863,131 B2 * | 1/2018 | Irwin ................ E03D 13/005 |
| 9,975,660 B2 * | 5/2018 | Cartledge ................ A47K 5/1201 |
| 10,183,801 B2 * | 1/2019 | Maalouf ................ B65D 83/0888 |
| 2004/0124101 A1 * | 7/2004 | Mitchell ................ B65D 83/0805 206/205 |
| 2006/0102508 A1 | 5/2006 | Decristofaro et al. |
| 2006/0180596 A1 | 8/2006 | Young et al. |
| 2006/0219812 A1 * | 10/2006 | Stephens ................ B65D 5/0227 239/302 |
| 2007/0148293 A1 * | 6/2007 | Lindsay ................ B65D 5/42 426/112 |
| 2007/0163895 A1 * | 7/2007 | Kirby ................ A45D 33/26 206/0.5 |
| 2007/0181594 A1 | 8/2007 | Thompson |
| 2007/0278242 A1 * | 12/2007 | Amundson ................ A47K 10/421 221/63 |
| 2009/0090737 A1 * | 4/2009 | Franco ................ A47K 5/12 221/96 |
| 2009/0206102 A1 | 8/2009 | Beck |
| 2012/0084909 A1 * | 4/2012 | Dunn ................ A47K 11/06 4/483 |
| 2012/0118909 A1 * | 5/2012 | Yaros ................ A47K 10/38 221/46 |
| 2012/0248136 A1 | 10/2012 | Meyers |
| 2012/0298686 A1 * | 11/2012 | Mothaffar ................ A47K 10/46 221/34 |
| 2013/0153597 A1 | 6/2013 | Hill et al. |
| 2013/0283740 A1 | 10/2013 | Eason |
| 2014/0305819 A1 | 10/2014 | Hill et al. |
| 2017/0296689 A1 * | 10/2017 | Peterson ................ A61L 9/122 |
| 2018/0148216 A1 * | 5/2018 | Stephens ................ B65D 5/542 |
| 2021/0000307 A1 * | 1/2021 | Venturino ................ A47K 10/32 |

OTHER PUBLICATIONS

Website Link: https://www.pinterest.com/pin/130534089171058424/ Downloaded Mar. 28, 2016 Toilet roll holder and air freshener dispenser.

Website Link: http://www.ebay.co.uk/itm/BENE-DOMO-STAINLESS-STEEL-CHROME-TOILET-PAPER-ROLL-AIR-FRESHENER-CAN-HOLDER-/111526918476 Downloaded Mar. 28, 2016 Bene Domo Stainless Steel Chrome Toilet Paper Roll Air Freshener Can Holder.

Website Link: http://irishmerchants.com/irishmerchants/Main/hygiene-Washroom.htm Downloaded Mar. 28, 2016 Washroom Ultimatic Paper Towel Dispenser System.

Website Link: http://www.sccans.com/towel-containers.htm Downloaded Nov. 21, 2015 Towel Containers (Wet Wipe Containers).

Website Link: http://zogics.com.au/dispensers-accessories/gym-wipes-dispenser-downward-dispensing-detail Downloaded Nov. 21, 2015 Downward Pull Dispenser.

Website Link: http://www.nicowetdry.com/Hybrid-Dispenser-Polished-Nickel-Starter-Pack_p_15.html Downloaded Jan. 21, 2015 Hybrid Dispenser Polished Nickel.

Website Link: http://www.freeismylife.com/2011/05/review-giveaway-cottonelle-flushable.html Downloaded Jan. 21, 2015 OneTouch Dispensing—wipes container hung on bathroom wall.

\* cited by examiner

US 11,272,817 B2

COMBINATION TOILET WIPES PACKAGE WITH ATTACHED AIR FRESHENER FOR USE WITH A DISPENSER CONFIGURED TO ACCEPT THE PACKAGE

FIELD OF THE INVENTION

This invention relates generally to packaging of moist toilet wipes, and more particularly to packages of moist toilet wipes that are configured for use with bathroom dispensers.

BACKGROUND OF THE INVENTION

Modern bathrooms having a toilet are known for having a toilet paper dispenser mounted to a wall conveniently near the toilet for supporting a roll of toilet paper within reach of a person using the toilet. However, sometimes one needs moisture to facilitate personal hygiene after using the toilet, and it is difficult to use the water from the sink while seated on the toilet. Accordingly, one must stand up from the toilet to moisten the toilet paper using water from the sink. Alternatively, one can use pre-moistened toilet wipes (also called flushable cleansing wipes) if some are within reach. Otherwise, one must get up from the toilet to gain access to the pre-moistened toilet wipes, if some are even available.

Modern bathrooms also often have some kind of air freshener device to cover up, neutralize, or otherwise reduce the sometimes unpleasant odors that are produced when using the toilet. However, these must be changed frequently enough such that they maintain their effectiveness. Often, one discovers that the air freshener device needs to be replenished only after it fails to perform its essential function. Also, they take up scarce space on either the toilet tank (if there is one), or on the cabinet that supports the sink (if there is one), most of the space being occupied by the sink itself.

SUMMARY OF THE INVENTION

The combination toilet wipes package with attached air freshener for use with a dispenser configured to accept the package provides a convenient refill of a dispenser for pre-moistened toilet wipes that are flushable, while also providing an air freshener that is conveniently replenished, without taking up space on the toilet, sink, or other existing bathroom surface.

A general aspect of the invention is a combination toilet wipes package that also freshens the air of a bathroom. The toilet wipes package includes: a toilet wipes package containing a plurality of moist toilet wipes; and an air freshener cartridge, in connected relationship with the toilet wipes package.

In some embodiments, the air freshener cartridge is attached to a side of the toilet wipes package.

In some embodiments, the air freshener cartridge includes an air baffle ring configured to engage air baffle slots.

In some embodiments, the toilet wipes package further includes a mounting, connected to both the toilet wipes package and the air freshener cartridge, so as to enable the air freshener cartridge to extend via the mounting from the toilet wipes package.

In some embodiments, the toilet wipes package further includes a mounting, connected to both the toilet wipes package and the air freshener cartridge, so as to enable the air freshener cartridge to extend further from the toilet wipes package into an air freshener compartment.

In some embodiments, the toilet wipes package includes: a slot for extracting wipes; and a peel-away wipes package seal applied over the slot so as to prevent the toilet wipes contained within the toilet wipes package from drying out.

In some embodiments, the air freshener cartridge includes: a hole for allowing air freshener to diffuse out of the air freshener cartridge into the room; and a peel-away air freshener cartridge seal applied over the hole so as to prevent air freshener from diffusing out of the air freshener cartridge until the peel-away air freshener cartridge seal is removed from the air freshener cartridge.

In some embodiments, the toilet wipes package includes: a slot for extracting wipes; and a peel-away wipes package seal applied over the slot so as to prevent the toilet wipes contained within the toilet wipes package from drying out, and the air freshener cartridge includes: a hole for allowing air freshener to diffuse out of the air freshener cartridge into the room; and a peel-away air freshener cartridge seal applied over the hole so as to prevent air freshener from diffusing out of the air freshener cartridge until the peel-away air freshener cartridge seal is removed from the air freshener cartridge, the peel-away wipes package seal and the peel-away air freshener cartridge seal being connected so as to form a combined wipes and air freshener seal, such that removing the combined wipes and air freshener seal both opens the package of moist toilet wipes so that wipes can be used, and opens the air freshener cartridge so as to enable the air freshener in the cartridge to diffuse into the room.

In some embodiments, an amount of air freshener contained in the air freshener cartridge will last at least as long as it would take a typical user to use the plurality of moist toilet wipes contained in the toilet wipes package.

In some embodiments, an amount of air freshener contained in the air freshener cartridge will last not much longer than it would take a typical user to use the plurality of moist toilet wipes contained in the toilet wipes package.

Another general aspect of the invention is a combination toilet wipes package that also freshens the air of a bathroom. This toilet wipes package includes: a toilet wipes package containing a plurality of moist toilet wipes, the toilet wipes package having an opening on a top side of the toilet wipes package for extracting moist toilet wipes from the toilet wipes package; and an air freshener cartridge attached to a side of the toilet wipes package other than the top side, the air freshener cartridge having a hole for allowing air freshener to diffuse out of the air freshener cartridge into the room.

In some embodiments, the air freshener cartridge includes an air baffle ring configured to engage air baffle slots.

In some embodiments, the combination toilet wipes package further includes: a mounting, connected to both the toilet wipes package and the air freshener cartridge, so as to enable the air freshener cartridge to extend via the mounting from the toilet wipes package.

In some embodiments, the combination toilet wipes package further includes: a mounting, connected to both the toilet wipes package and the air freshener cartridge, so as to enable the air freshener cartridge to extend further from the toilet wipes package into an air freshener compartment of a toilet wipes dispenser.

In some embodiments, the toilet wipes package includes: a peel-away wipes package seal applied over the opening of the toilet wipes package so as to prevent the toilet wipes contained within the toilet wipes package from drying out until the combination toilet wipes package is ready for use.

In some embodiments, the air freshener cartridge includes: a peel-away air freshener cartridge seal applied over the hole of the air freshener cartridge so as to prevent air freshener from diffusing out of the air freshener cartridge until the peel-away air freshener cartridge seal is removed from the hole of the air freshener cartridge.

In some embodiments, the toilet wipes package includes: a peel-away wipes package seal applied over the opening of the toilet wipes package so as to prevent the toilet wipes contained within the toilet wipes package from drying out until the combination toilet wipes package is ready for use, and wherein the air freshener cartridge includes: a peel-away air freshener cartridge seal applied over the hole of the air freshener cartridge so as to prevent air freshener from diffusing out of the air freshener cartridge until the peel-away air freshener cartridge seal is removed from the hole of the air freshener cartridge, the peel-away wipes package seal and the peel-away air freshener cartridge seal being connected so as to form a combined wipes and air freshener seal, such that removing the combined wipes and air freshener seal both opens the package of moist toilet wipes so that wipes can be used, and opens the air freshener cartridge to enable the air freshener in the cartridge to diffuse into the room.

In some embodiments, an amount of air freshener contained in the air freshener cartridge will last at least as long as it would take a typical user to use the plurality of moist toilet wipes contained in the toilet wipes package.

In some embodiments, an amount of air freshener contained in the air freshener cartridge will last not much longer than it would take a typical user to use the plurality of moist toilet wipes contained in the toilet wipes package.

In some embodiments, a scent added to the moist toilet wipes contained in the toilet wipes package matches the scent of the air freshener in the air freshener cartridge.

BRIEF DESCRIPTION OF THE DRAWINGS

Many additional features and advantages will become apparent to those skilled in the art upon reading the following description, when considered in conjunction with the accompanying drawings, wherein.

DETAILED DESCRIPTION

Figure 1:
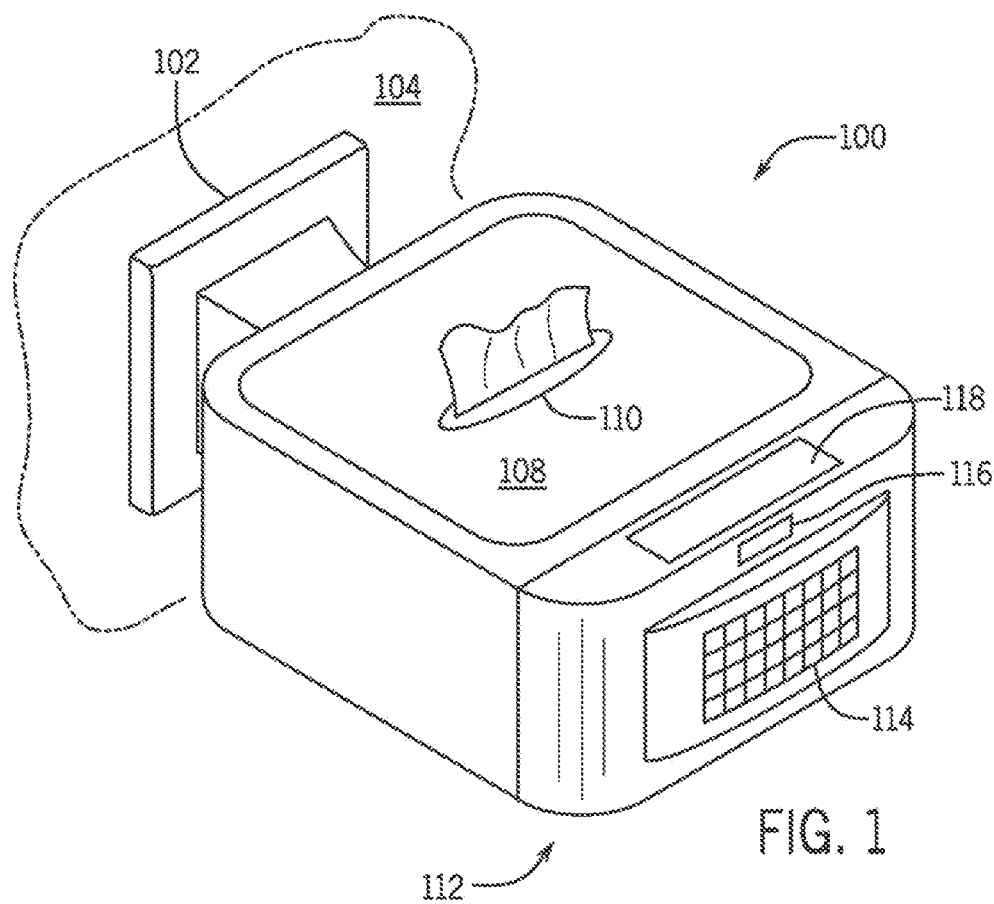
FIG. 1 is a perspective front view of the wall-mountable wipes dispenser with integrated air freshener.

FIG. 1 shows a wall-mountable toilet wipes dispenser 100, a wall fastener 102, attached to a wall 104, a toilet wipes dispensing section 106, a wipes compartment lid 108, having an opening 110 for extracting wipes, an air freshener section 112, having a vent 114, a button 116, and an air freshener compartment lid 118.

The wall-mountable toilet wipes dispenser 100 has a wall fastener 102 that mounts to the wall 104 at a location near a toilet. The dispenser includes the toilet wipe dispensing compartment 200 (see FIG. 2) which is adapted to contain a package of moist toilet wipes (not shown), such as rectangular packages of moist toilet wipes presently available. The package of moist toilet wipes should have an opening or slot that would align generally with the opening 110 in the lid 108, through which the toilet wipes can be dispensed.

The wall-mountable toilet wipes dispenser 100 also includes an air freshener section 112 having and air freshener compartment 119 capable of containing an air freshener cartridge 202 which releases air freshener (also see FIG. 7) through the vent 114 on the front of the air freshener section 112. When the button 116 is pressed, it opens the air freshener cartridge lid 118 when it is time to replace the air freshener cartridge 202.

Figure 2:
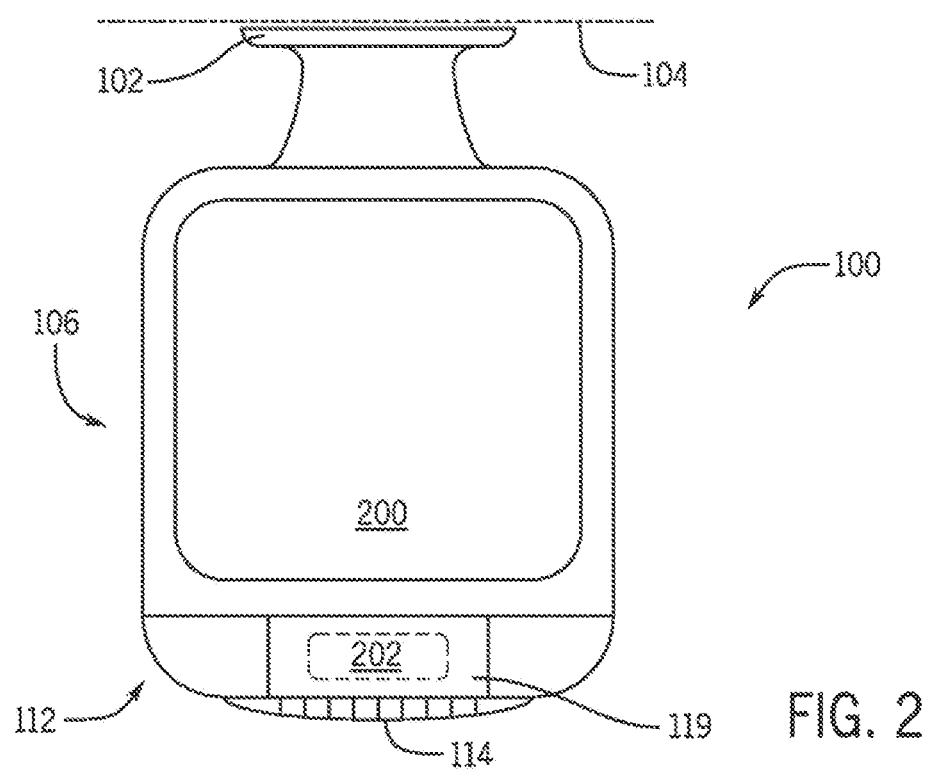
FIG. 2 is a top cross-sectional view of a dispenser having separate compartments for wipes and air freshener, showing the inside of the dispenser of FIG. 1.

FIG. 2 shows a cross-sectional top view of the dispenser 100 of FIG. 1, revealing the compartment 200 for receiving a rectangular package of wipes of a size and shape that generally fills the compartment 200. Also shown is the wall fastener 102 attached to the wall 104.

The wall fastener 102 supports the toilet wipe dispensing section 106 and the integrated air freshener section 112, so as to dispense the toilet wipes at a convenient wall 104 location near a toilet.

The integrated air freshener section 112 includes the air freshener cartridge compartment 119 which receives the air freshener cartridge 202, which releases air freshener via the controllable vent 114.

Figure 3:
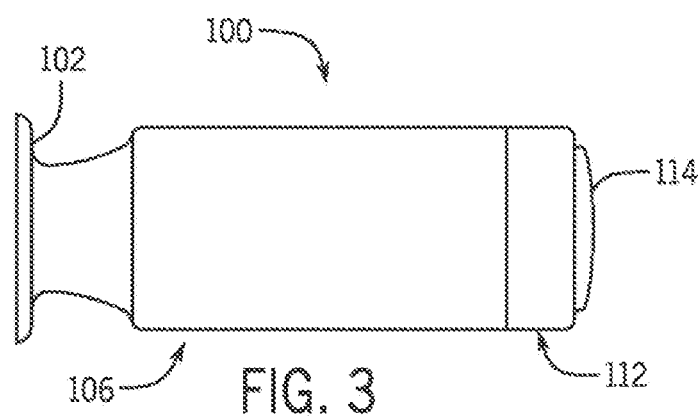
FIG. 3 is a side view of the dispenser of FIG. 1.

FIG. 3 shows a side view of the wall-mountable toilet wipes dispenser 100, the wall fastener 102, the toilet wipe dispensing section 106, and the air freshener section 112 having a vent 114.

Figure 4:
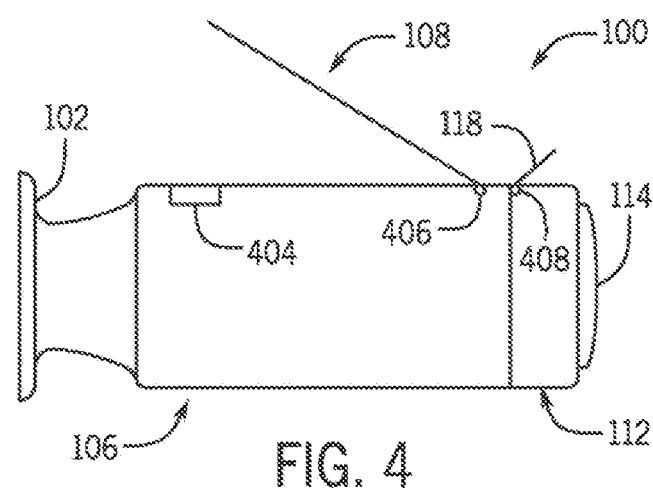
FIG. 4 is a side view of the dispenser of FIG. 1 showing the wipes lid in an open position and the air freshener cartridge lid in an open position.

FIG. 4 shows a side view of the wall-mountable toilet wipes dispenser 100, supported by the wall fastener 102. The toilet wipe dispensing section 106 includes a wipes compartment lid 108, and the air freshener section 112 includes an air freshener compartment lid 118.

The air freshener compartment lid 118 rotates on an air freshener hinge 408. In a similar manner, the wipes compartment lid 108 rotates on the wipes hinge 406. The wipes compartment lid 108 locks into place using the wipe compartment latch 404 which is located opposite from the wipes hinge 406.

The side view of FIG. 4 shows the wipes compartment lid 108 in an open position, and shows the air freshener compartment lid 118 in an open position.

Figure 5:
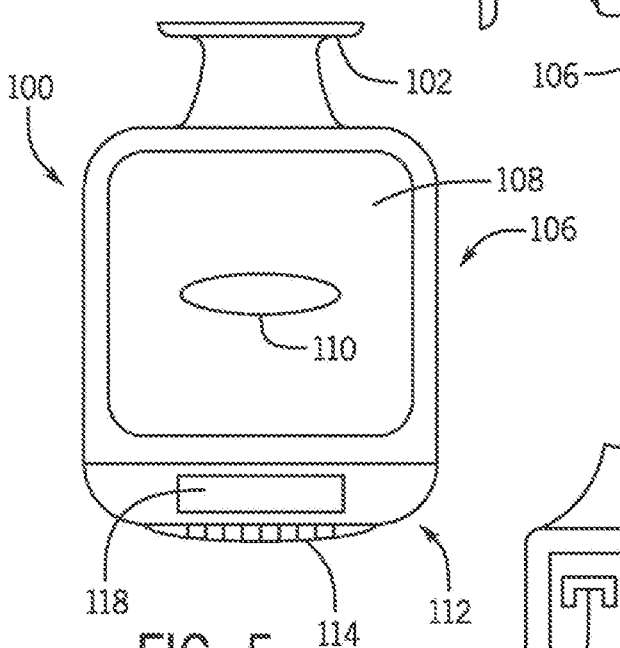
FIG. 5 is a top view of the dispenser showing an opening for allowing a toilet wipe to be pulled out.

FIG. 5 shows top view of the wall-mountable toilet wipes dispenser 100, and the wall fastener 102. It can be seen that the dispenser 100 includes a toilet wipes dispensing section 106, and an air freshener section 112. The wipes dispensing section 106 includes a wipes lid 108, having an opening 110 for pulling out individual moist toilet wipes from the refill package (not shown) under the wipes lid 108. The air freshener section 112 includes an air freshener lid 118 that keeps air freshener confined to the air freshener section until released into the room via the vent 114.

Figure 6:
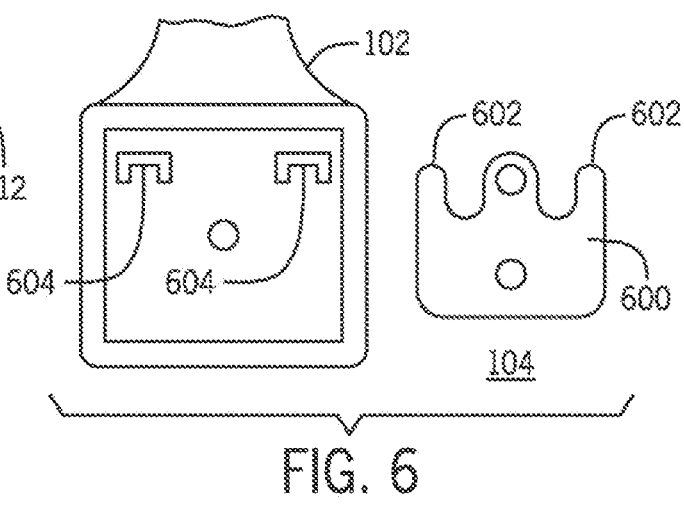
FIG. 6 is a rear view of the dispenser of FIG. 1 showing a two-prong receiver, and the cooperative wall mount having two prongs for mounting the dispenser on a wall.

FIG. 6 shows a rear of the wall fastener 102, having two tabs 604. The two tabs 604 engage with the two prongs 602 of the two-prong receiver 600, which is attachable to the wall 104. In this embodiment, the wall fastener 102 is mounted on the wall 104 using the two-prong receiver 600. The two-prong receiver 600 is attached to the wall 104 by using a fastening device such as a nail or a screw (not shown), and the two-prong receiver 600 has two prongs 602 which cooperate with two tabs 604 on the back of the wall fastener 102 to hold the wall fastener 102 firmly to the wall 104.

Figure 7:
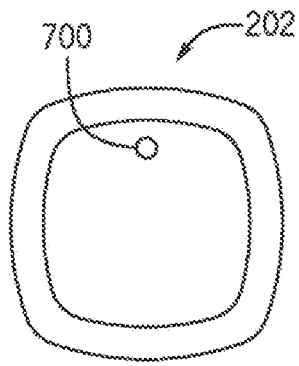
FIG. 7 is a front view of an air freshener cartridge for use in the dispenser of FIG. 2.

FIG. 7 shows an air freshener cartridge 202, having a hole 700 for allowing air freshener to diffuse out of the air freshener cartridge 202 into the room.

Figure 8:
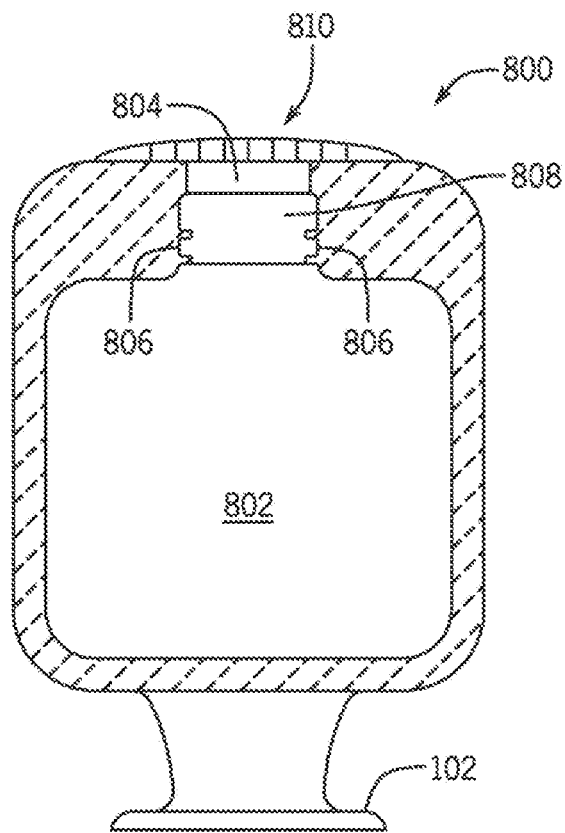
FIG. 8 is a top cross-sectional view of a dispenser having a single compartment shaped to accommodate an integrated dispensing package of moist toilet wipes also having an integrated air freshener cartridge.

FIG. 8 shows a top cross-sectional view of an empty wall-mountable toilet wipes dispenser 800 having a toilet wipes package compartment 802. When a refill wipes package 900 is not in the dispenser 800, air can flow from the wipes package compartment 802 towards the region vented to the outside 804, past the air baffle slots 806 and through the air freshener compartment 808, and out via the adjustable vent 810. Thus, the air freshener compartment 808 is in air flow communication with the toilet wipe package compartment 802, when a refill wipes package 900 is not in the dispenser 800.

Figure 9A:
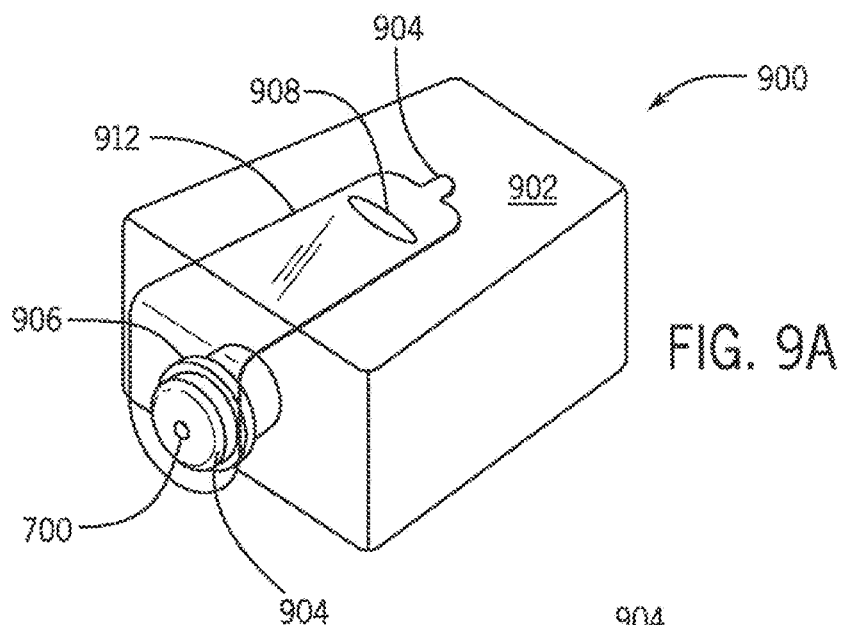
FIG. 9A is an isometric view of an integrated dispensing package of FIG. 9, having a peel-away seal covering the openings of both the wipes package and the air freshener cartridge.
Figure 9:
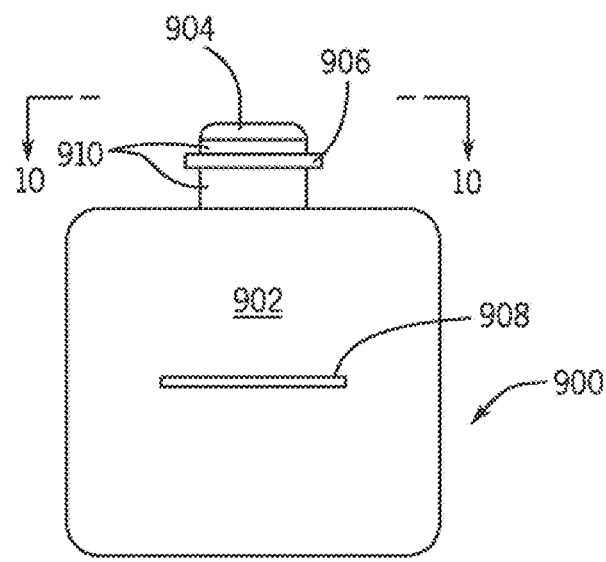
FIG. 9 is a top view of an embodiment of an integrated dispensing package of moist toilet wipes having an integrated air freshener cartridge for use with the dispenser of FIG. 8.

In this embodiment, the wall-mountable toilet wipes dispenser 800 is shaped to hold an integrated air freshener cartridge, as shown in FIG. 9. Within the wall mountable toilet wipes dispenser 800 there are two compartments: the toilet wipe package compartment 802 and the air freshener compartment 808. Between the two compartments are the air baffle slots 806 which help prevent the contents of the air freshener cartridge 904 from entering the toilet wipe package compartment 802. Also shown are the region vented to the outside 804, through which the air freshener is dispensed from the cartridge 904, and the adjustable vent 810 which controls the release of the air freshener from the cartridge 904.

Figure 13:
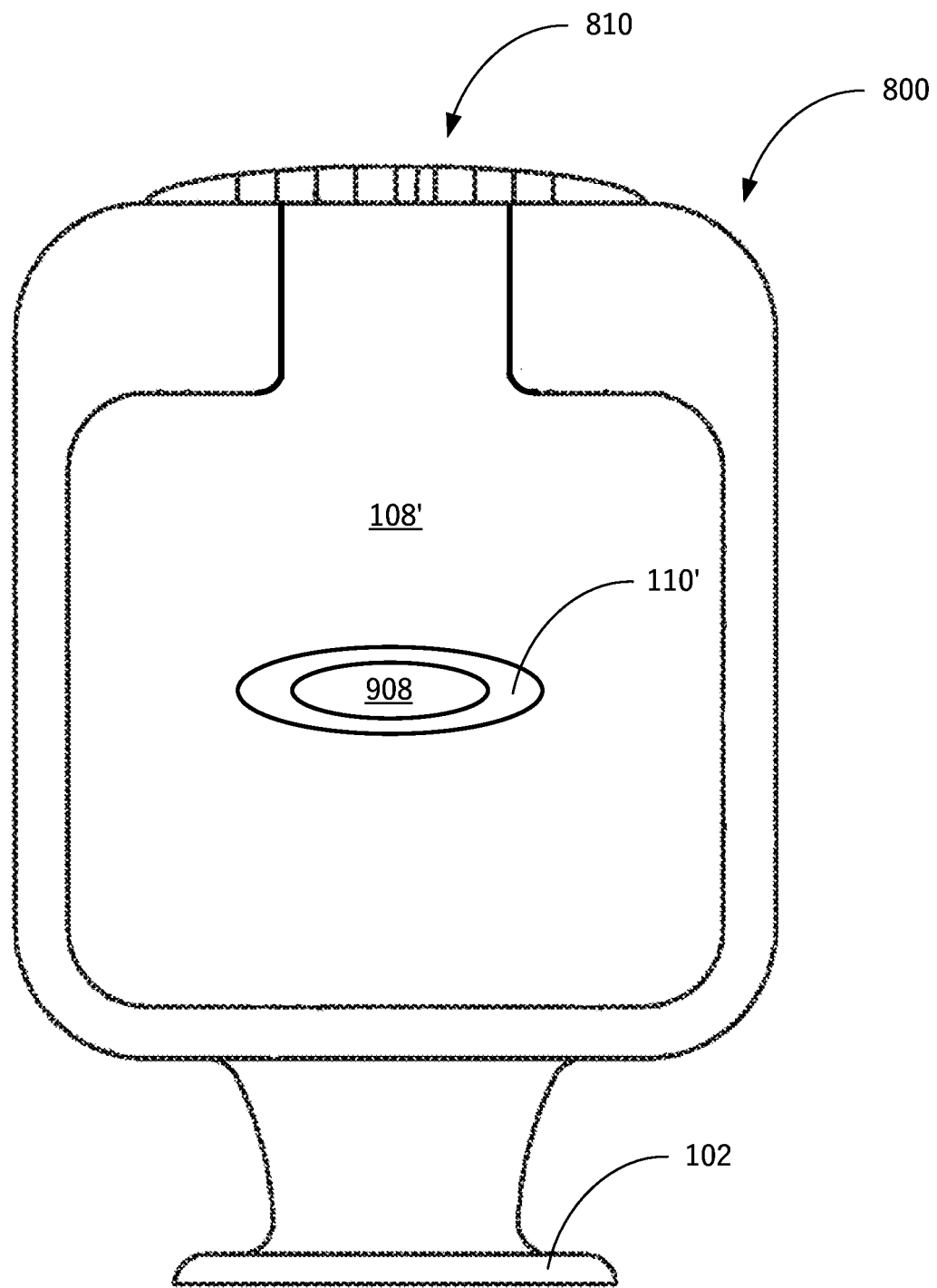
FIG. 13 is a top view showing the integrated dispensing package of moist toilet wipes having a single lid that encloses the entire space encompassing both the integrated air freshener cartridge compartment and the single compartment shaped to accommodate the package of moist toilet wipes.

The wipes dispenser 800 also includes a wipes lid 108' (shown in FIG. 13), such as the one shown in FIG. 1, having an opening 110 for dispensing wipes like the wipes lid 108, but also extending over and covering the air freshener compartment 808, such that when the wipes lid 108' is closed, it closes both the toilet wipe package compartment 802 and the air freshener compartment 808. Thus, in this embodiment, a separate air freshener cartridge lid 118 is not needed.

When closed, this lid 108' also cooperates with the air baffle ring 906, which when inserted into the air baffle slots 806, prevents the contents of the air freshener cartridge 904 from entering the toilet wipe package compartment 802, so that the adjustable vent 810 effectively controls release of air freshener into the room.

In FIG. 9, a top view is shown of the integrated dispensing (or refill) package 900 which includes a toilet wipe dispensing package 902 having a wipes dispensing slot 908 for dispensing toilet wipes, an air freshener cartridge 904 (similar to the air freshener cartridge 202) mounted on a mounting block 910, and an air baffle ring 906 attached to the mounting block 910.

The air baffle ring 906, when inserted into the air baffle slots 806 (FIG. 8) prevents the contents of the air freshener cartridge 904 from entering the toilet wipe package compartment 802. The wipes dispensing slot 908 is a slot through which wipes are pulled.

FIG. 9A shows an isometric view of the integrated dispensing package 900, which includes a toilet wipe dispensing package 902, an air freshener cartridge 904 having a hole 700 for releasing air freshener into the room, and an air baffle ring 906. Before use, the integrated dispensing package 900 includes a peel-away seal 912 applied over the opening 908 of the toilet wipes package 902 so as to prevent the toilet wipes contained within the toilet wipes package 902 from drying out until the combination toilet wipes package is ready for use.

The peel-away seal 912 is also applied over the opening 700 of the air freshener cartridge 904 so as to prevent air freshener from diffusing out of the air freshener cartridge 904 until the peel-away seal 912 is removed from the hole 700 of the air freshener cartridge 904.

In this embodiment, the peel-away seal 112 covers both the opening 908 of the toilet wipes package 902 and the opening 700 of the air freshener cartridge 904. In other embodiments, a separate peel-away seal could be used to separately seal the opening 908 of the toilet wipes package 902 and the opening 700 of the air freshener cartridge 904.

Before using the integrated dispensing package 900, the seal 912 would be peeled off using the tab 914, thereby uncovering both the opening 908 of the toilet wipes package 902 and the opening 700 of the air freshener cartridge 904. Thus, removing the seal 912 both opens the package of moist toilet wipes 902 so that wipes can be used, and opens the air freshener cartridge 904 to enable the air freshener in the cartridge 904 to diffuse into the room.

Figure 10:
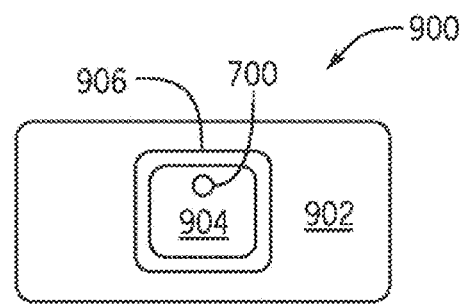
FIG. 10 is a front view of the integrated dispensing package of moist toilet wipes having an integrated air freshener cartridge of FIG. 9.

FIG. 10 shows a front view of an integrated dispensing package 900, which includes a toilet wipe dispensing package 902, an air freshener cartridge 904 having a hole 700 for releasing air freshener into the room, and an air baffle ring 906.

Figure 11:
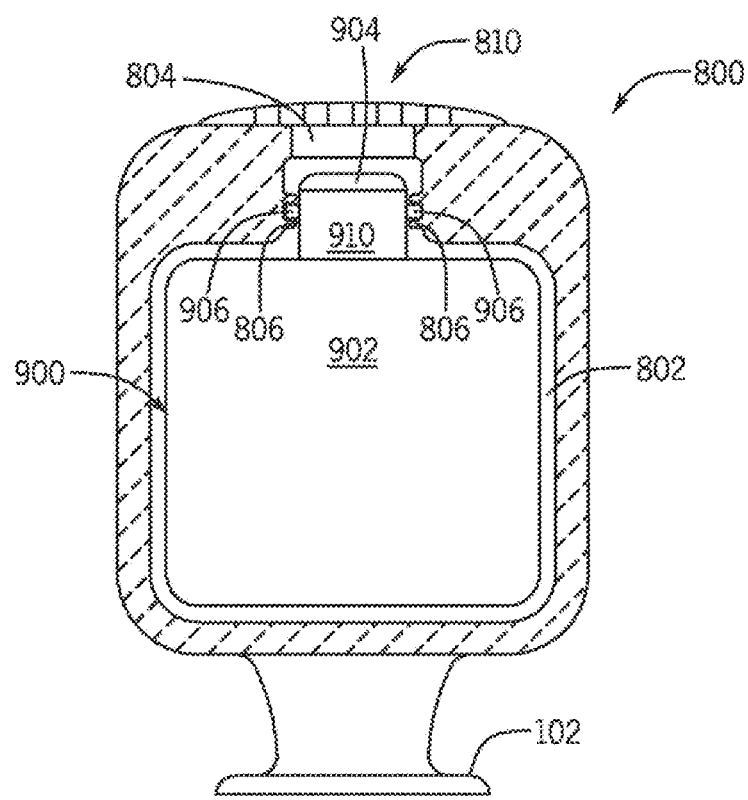
FIG. 11 is a top cross-sectional view showing the integrated dispensing package of moist toilet wipes having an integrated air freshener cartridge inserted into the single compartment shaped to accommodate the package of moist toilet wipes having an integrated air freshener cartridge of FIG. 9.

FIG. 11 shows top cross-sectional view of the wall-mountable toilet wipes dispenser 800, having an integrated moist wipes package 900 inserted therein. The wipes package 902 rests within the toilet wipe package compartment 802, the air freshener cartridge 904 rests within the region 804 which is vented to the room via the adjustable vent 810.

The air baffle ring 906 engages with the air baffle slots 806 so as to ensure that air freshener from the air freshener cartridge 904 is emitted from the dispenser 800 at a rate substantially controllable using the adjustable vent 810. Both the air baffle ring 906 and the air freshener cartridge 904 are mounted on the mounting block 910 which is attached to the wipes package 902.

The integrated dispensing package 900 is an integrated unit, combining the toilet wipe dispensing package 902 and the air freshener cartridge 904 as one combined package. The package also includes the air baffle ring 906. When the integrated dispensing package 900 is inserted into the wall-mountable toilet wipes dispenser 800, the air baffle ring 906 fits snugly into the air baffle slots 806, preventing the contents of the air freshener cartridge from entering the toilet wipe package compartment 802 such that most of the air freshener exits the dispenser 800 via the region vented to the outside 804, and via the adjustable vent 810, thereby controllably releasing the air freshener into the room.

Figure 12:
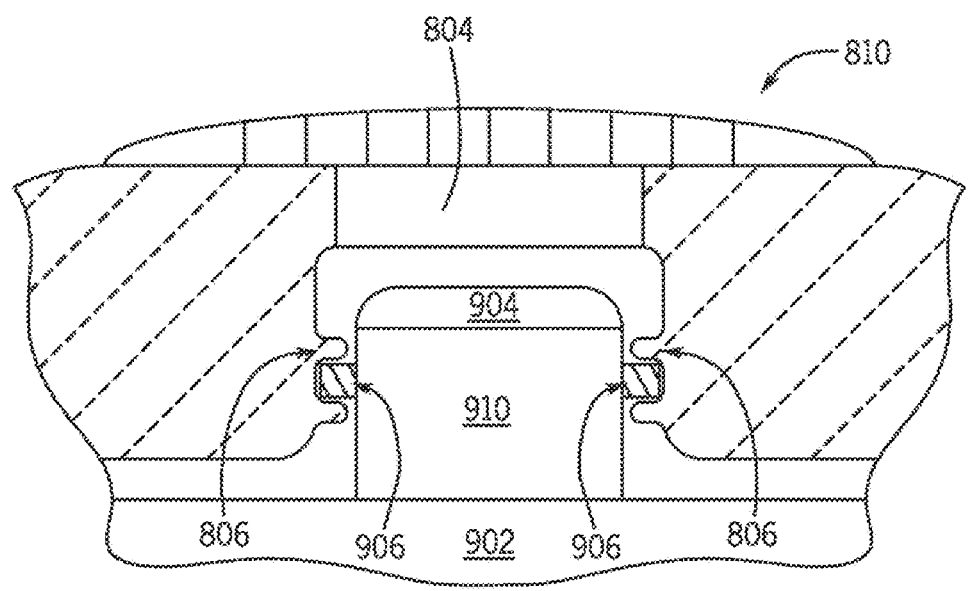
FIG. 12 is a close-up top cross-sectional view of FIG. 11 showing a cooperative air barrier that serves to prevent air freshener from the air freshener cartridge from entering the portion of the single compartment that contains the moist toilet wipes.

FIG. 12 shows a close-up top cross-sectional view of an integrated dispensing (refill) package 900 inserted into the dispenser 800 as shown in FIG. 11. The air freshener cartridge 904 is mounted on a mounting block 910, which is attached to the package of wipes 902, so that the air freshener cartridge 904 is placed in the region 804 which is vented to the outside via the adjustable vent 810. The air baffle slots 806 receive the air baffle ring 906, which is shaped so as to fit snugly into the air baffle slots 806, and engage with the lid 108' (not shown) thereby substantially preventing air freshener from the air freshener cartridge 904 from leaking into the compartment 802 so that the adjustable vent 810 substantially controls the release rate of air freshener into the room.

Other modifications and implementations will occur to those skilled in the art without departing from the spirit and the scope of the invention as claimed. Accordingly, the above description is not intended to limit the invention, except as indicated in the following claims.

What is claimed is:

1. A toilet wipes and air freshener dispensing system comprising:
    a toilet wipes refill package including:
        a package volume, defined by the refill package, and configured to contain a supply of moistened toilet wipes, and a package opening configured to permit the toilet wipes to be removed from the volume therethrough; and
        a mounting, integrated with the package and extending from the package to a distal end, the mounting configured to support an air freshener cartridge coupled to the distal end, the mounting including an air baffle ring disposed between the air freshener cartridge and the package; and
    a refillable dispenser configured to house the refill package, the refillable dispenser including:
        a dispenser housing defining a contiguous housing volume configured to receive and contain the refill package through an opening in the housing, the contiguous volume including a first portion configured to receive and contain the supply of toilet wipes within the package volume of the refill package therein, and a second portion, formed of interior sidewalls, and which is configured to receive and contain the distal end of the mounting and the air freshener cartridge coupled thereto;
        a lid configured to cover the housing opening, the lid including a dispenser slot opening; and
        a vent opening configured to be in airflow communication with ambient air outside of the dispenser and with the second portion of the contiguous volume,
    wherein the refill package and the dispenser are configured so that when the refill package is received by the dispenser and the lid is closed:
        the dispenser slot and the refill package openings are configured to align with one another, thereby permitting toilet wipes to be dispensed from the refill package through the dispenser slot opening, and
        the baffle ring of the mounting is configured to sealably cooperate with slots in the sidewalls defining the second portion and with the closed lid, to thereby prevent airflow communication between the first and second portions so that the air freshener is only dispensed into the ambient air through the vent opening.

2. The system of claim 1, wherein the supply of toilet wipes is pre-moistened, the air freshener cartridge includes an opening through which air freshener diffuses from the air freshener cartridge into the ambient air, and the toilet wipes refill package further includes:
    a peel-away wipes package seal, configured to be applied to the package opening to prevent the supply of toilet wipes from drying out, and
    a peel-away air freshener cartridge seal, configured to be applied to the air freshener cartridge opening, thereby preventing the air freshener from diffusing out of the air freshener cartridge,
    wherein just before the refill package is received by the dispenser housing, the peel-away wipes package seal is removed from the package opening to permit the toilet wipes to be dispensed and the peel-away air freshener cartridge seal is removed from the air freshener cartridge opening to permit the air freshener to be dispensed therethrough.

3. The system of claim 2 wherein the peel-away wipes package seal and the peel-away air freshener cartridge seal are formed as a single integrated peel-away seal.

4. The system of claim 1 wherein the lid is hingedly coupled along one edge to a top surface of the housing to permit the lid to be hingedly opened to provide access to the contiguous volume of the housing through the housing opening.

5. The system of claim 1 wherein the dispenser housing is configured to be coupled to a wall surface.

6. The system of claim 1 wherein a predetermined amount of air freshener is contained within the cartridge sufficient to last approximately as long as the supply of toilet wipes.

* * * * *